(12) United States Patent
Tsuboi et al.

(10) Patent No.: US 6,580,949 B1
(45) Date of Patent: Jun. 17, 2003

(54) IMPLANTABLE ELECTRODE LEAD

(75) Inventors: Fuminori Tsuboi, Nakai-machi (JP); Katsuhiro Shirakawa, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 117 days.

(21) Appl. No.: 09/620,988

(22) Filed: Jul. 20, 2000

(30) Foreign Application Priority Data

Jul. 23, 1999 (JP) .............................. 11-209717

(51) Int. Cl.[7] ................................. A61N 1/05
(52) U.S. Cl. .................. 607/125; 607/119; 607/122; 607/126
(58) Field of Search .............. 600/372–384, 600/393, 394; 607/122, 119, 125, 126

(56) References Cited

U.S. PATENT DOCUMENTS

| | | |
|---|---|---|
| 4,402,328 A | 9/1983 | Doring |
| 4,454,888 A | 6/1984 | Gold |
| 5,796,044 A | 8/1998 | Cobian et al. |
| 6,083,216 A * | 7/2000 | Fischer, Sr. .............. 600/374 |
| 6,253,111 B1 * | 6/2001 | Carner .................... 600/373 |
| 6,289,250 B1 * | 9/2001 | Tsuboi et al. ............ 607/122 |

FOREIGN PATENT DOCUMENTS

| | | |
|---|---|---|
| JP | 5-49701 | 3/1993 |
| JP | 11-333000 | 12/1999 |

* cited by examiner

Primary Examiner—George R. Evanisko
Assistant Examiner—Omar Khan
(74) Attorney, Agent, or Firm—Burns, Doane, Swecker & Mathis, LLP

(57) ABSTRACT

A flexible, thin implantable electrode lead can maintain a desired portion of a lead body (14) in a desired shape conforming to a body portion. The lead body (14) includes a conductor coil (30) obtained by helically winding at least one insulation-coated electrical conduction conductor wire, an insulating sheath (32) made of an electrically insulating resin material and covering the outer surface of the conductor coil, and a flexible reinforcing tube (40) formed to deform into a desired shape in the cavity of the conductor coil.

14 Claims, 6 Drawing Sheets

IMPLANTABLE ELECTRODE LEAD

FIELD OF THE INVENTION

The present invention relates to an implantable electrode lead and, more particularly, to a technique for forming a predetermined portion of the lead body of an atrial lead into a desired shape such as a "J" shape in order to use the implantable electrode lead together with, e.g., a heart pacemaker or implantable defibrillator.

BACKGROUND OF THE INVENTION

Many conventional implantable electrode leads used together with heart pacemakers and implantable defibrillators are known. An implantable electrode lead is generally comprised of at least one electrode for supplying an electrical stimulation pulse or sensing an electrical evoked response of the heart, an electrical connector for connecting the electrode lead to a heart pacemaker or implantable defibrillator, and a lead body inserted between the electrode and the electrical connector and made up of a biocompatible insulating sheath and a conductor coil for transmitting an electrical signal between the electrode and the heart pacemaker or implantable defibrillator.

In an electrode lead for cervical vein, the distal-end electrode is indwelled in the heart via the vein, and the proximal-end electrode is connected to the connection housing of the heart pacemaker or implantable defibrillator. The implantable electrode leads are classified into atrial and ventricular leads. The ventricular lead electrode is generally indwelled in the apex of the right ventricle, while the atrial lead electrode is generally indwelled in the right atrial auricle. The atrial lead has a J-shaped portion near its distal end to facilitate indwelling of the electrode in the auricle. A general means for imparting the J shape to the atrial lead is comprised of an insulating sheath or conductor coil serving as a constituent element of the lead body. As a means for imparting the J shape to the atrial lead, a separate reinforcing member is disposed to impart the J shape or to hold the J shape in one or both of the insulating sheath and the conductor coil. The implantable electrode lead has a cavity for receiving a stylet. When the stylet reaches the J-shaped portion at the distal end of the atrial lead, the distal end of the atrial lead follows the shape of the distal end of the stylet. When the stylet is retracted to the proximal-end side, the distal end of the atrial lead restores the J shape. The atrial lead electrode is indwelled in the atrial auricle using such stylet movement.

Imparting a desired shape to the implantable electrode lead is not limited to the J shape of the atrial lead. Japanese Patent Laid-Open No. 5-49701 to Nakajima discloses a technique for forming a special shape such as a desired helical shape in the lead body.

SUMMARY OF THE INVENTION

As one of the state-of-the-art means for imparting the J shape to an atrial lead, the J shape is imparted to a constituent element of a lead body. To increase the rigidity of the insulating sheath or conductor coil, however, the outer diameter of the lead body increases, and flexibility of the whole lead body degrades. An increase in outer diameter of the lead body may cause hemostasis. The lack of flexibility of the lead body increases the mechanical stress inflicted on a living body by the lead body.

It is difficult to obtain a sufficient retaining force for maintaining the J shape in a thin flexible silicone atrial lead. It is therefore considerably difficult to indwell the electrode in the atrial auricle. According to the conventional method of imparting the J shape to a constituent element of a lead body, when a lead structure described in Japanese Patent Laid-Open No. 11-333000 proposed to improve the durability of the lead body is applied to an atrial lead, it is difficult to obtain a sufficient retaining force for maintaining the J shape.

For example, U.S. Pat. No. 4,454,888 discloses a case in which a metal wire is used as a separate reinforcing means to reinforce the J shape. According to this disclosure, when the metal wire breaks, the metal wire bores into the insulating sheath to the outside, thus posing problems as to safety and reliability.

The present invention has been made in consideration of the conventional problems described above, and has as its object to provide an implantable electrode lead which can have a small diameter with flexibility and can maintain a desired portion of a lead body to a desired shape conforming to a predetermined portion of a living body.

In order to solve the conventional problems described above and achieve the above object, according to the present invention, an implantable electrode lead having a lead body for performing at least one of transmission of an electrical stimulation pulse generated by an implantable device to a living body and transmission of an electrical signal from the living body to the implantable device, the lead body having at least one electrode at a distal end thereof, and connector for mechanically and electrically connecting a proximal position of the lead body to the implantable device, characterized in that the lead body comprises a conductor coil obtained by helically winding at least one insulation-coated electrical conduction conductor wire and an insulating sheath made of an electrically insulating resin material to cover an outer surface of the conductor coil, and a flexible reinforcing tube shaped to deform into a desired shape is disposed in a cavity of the conductor coil, thereby maintaining a predetermined portion of the lead body in the desired shape.

According to an aspect of the implantable electrode lead of the present invention, the implantable electrode lead is characterized in that the predetermined portion is located near a distal end of the lead body, and the desired shape is a substantially J shape.

According to another aspect of the implantable electrode lead of the present invention, the implantable electrode lead is characterized in that the reinforcing tube is made of a predetermined resin material containing polyimide.

According to still another aspect of the implantable electrode lead of the present invention, the implantable electrode lead is characterized in that rigidity of the reinforcing tube is higher than rigidity of a combination of the coil and the insulating sheath.

According to still another aspect of the implantable electrode lead of the present invention, the implantable electrode lead is characterized in that the reinforcing tube is formed into the desired shape beforehand prior to assembly.

According to still another aspect of the implantable electrode lead of the present invention, the implantable electrode lead is characterized in that after the reinforcing tube is disposed in the cavity of the coil in a straight state, the reinforcing tube is shaped to obtain the desired shape.

According to still another aspect of the implantable electrode lead of the present invention, the implantable electrode lead is characterized in that the distal end of the reinforcing tube is connected to the electrode, and a proximal end of the reinforcing tube is connected to the connector.

According to still another aspect of the implantable electrode lead of the present invention, the implantable electrode lead is characterized in that the lead body has a size of not more than 2 mm, the insulating sheath is made of an electrically insulating, flexible resin material having a Shore hardness of less than 80 A, and the conductor coil has a spring index D/d (average diameter of coil/diameter of conductor wire) of more than 7.8.

According to still another aspect of the implantable electrode lead of the present invention, the implantable electrode lead is characterized in that the conductor coil comprises a multi-wire coil obtained by winding a plurality of insulation-coated conductor wires in the same average diameter.

According to still another aspect of the implantable electrode lead of the present invention, the implantable electrode lead is characterized in that the conductor wire comprises a multi-wire coil and the electrode is divided into a plurality of electrode portions such that one of wires of the multi-wire coil transmits one electrical signal and remaining ones of the multi-wire coil transmit remaining electrical signals.

According to still another aspect of the implantable electrode lead of the present invention, the implantable electrode lead is characterized in that an insulation coating of the conductor coil is made of fluoroplastic.

According to still another aspect of the implantable electrode lead of the present invention, the implantable electrode lead is characterized in that the conductor wire has a composite or cladding structure of a first metal material having a low resistivity and a second metal material excellent in corrosion resistance and mechanical characteristics.

According to still another aspect of the implantable electrode lead of the present invention, the implantable electrode lead is characterized in that a cavity for receiving a straight stylet is formed in the reinforcing tube, the stylet is inserted into the cavity to deform the desired shape of the predetermined portion of the lead body into a linear shape, and the desired shape is then restored by removing the stylet.

According to still another aspect of the implantable electrode lead of the present invention, the implantable electrode lead is characterized in that the implantable electrode lead is applicable to the implantable electrode lead described in Japanese Patent Laid-Open No. 11-333000, and a flexible reinforcing tube formed into a desired shape is disposed in the cavity of the coil to form the predetermined portion of the lead body in the desired shape.

With the above arrangements, a flexible, thin implantable electrode lead can provide reinforcing means for forming the predetermined portion of the lead body into a desired shape. Since the reinforcing means is comprised of a tube and disposed in the cavity of the coil, a danger of the reinforcing means boring into the insulating sheath to the outside can be prevented. In addition, when the reinforcing means is imparted with, e.g., the J shape of an atrial lead, the atrial lead can have better operability. Movement and removal of the electrode upon surgical operation can be prevented.

Other features and advantages of the present invention will be apparent from the following description taken in conjunction with the accompanying drawings, in which like reference characters designate the same or similar parts throughout the figures thereof.

DETAILED DESCRIPTION OF THE PREFERRED EMBODIMENTS

Preferred embodiments of the present invention will be described in detail with reference to the accompanying drawings.

[First Embodiment]

This embodiment exemplifies a case in which the structure of an implantable electrode lead of the present invention is applied to the J shape generally formed near the distal end of an atrial lead. The present invention is not limited to this. An arbitrary shape can be set in any portion.

Figure 1:
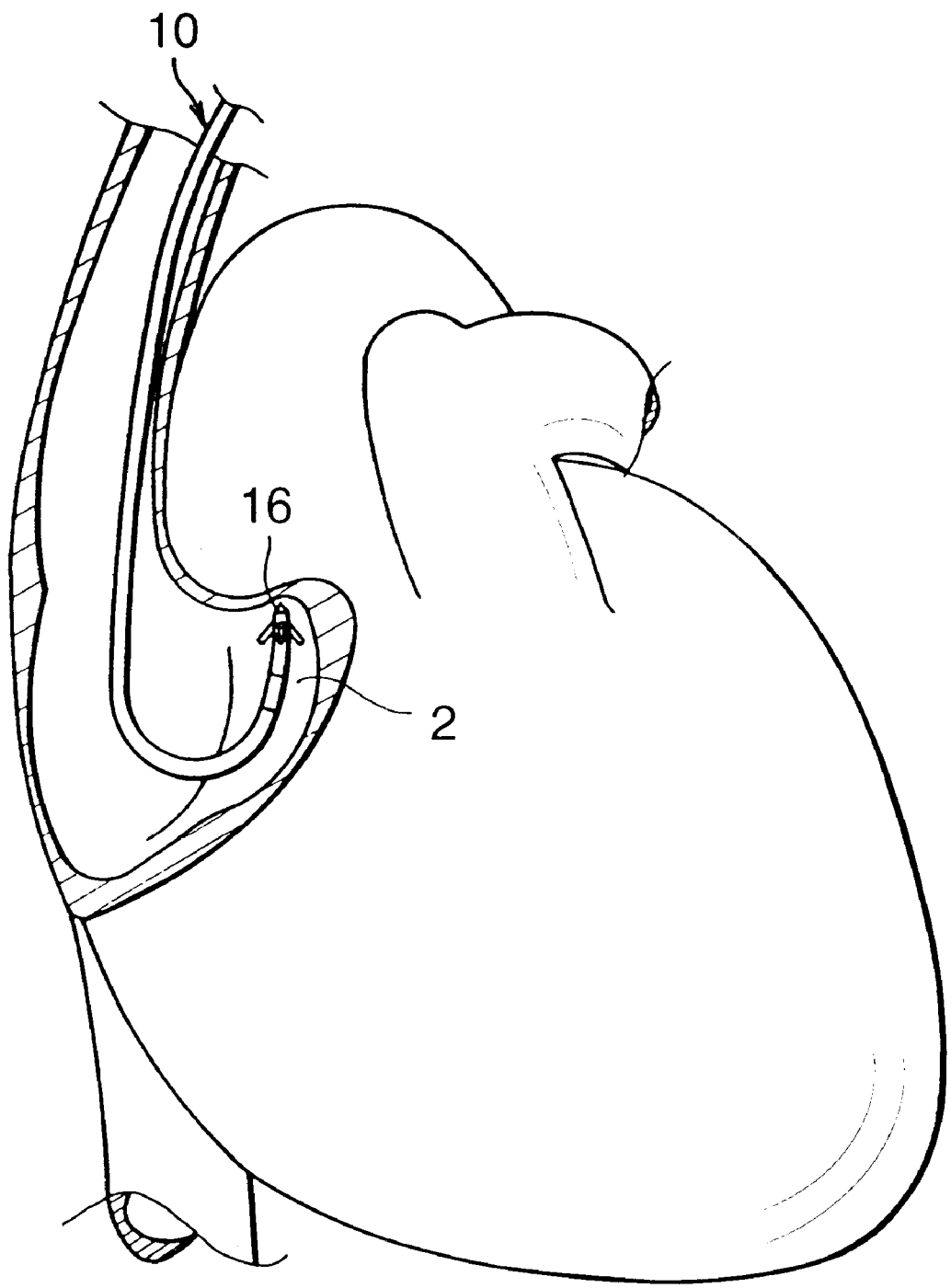
FIG. 1 is a view showing a state in which an implantable electrode lead (atrial lead) is indwelled in the atrium.

FIG. 1 shows a state in which an atrial lead 10 as the implantable electrode lead is indwelled in the atrium. As shown in FIG. 1, a tip electrode 16 of the atrial lead 10 is indwelled in a right atrial auricle 2.

Figure 2:
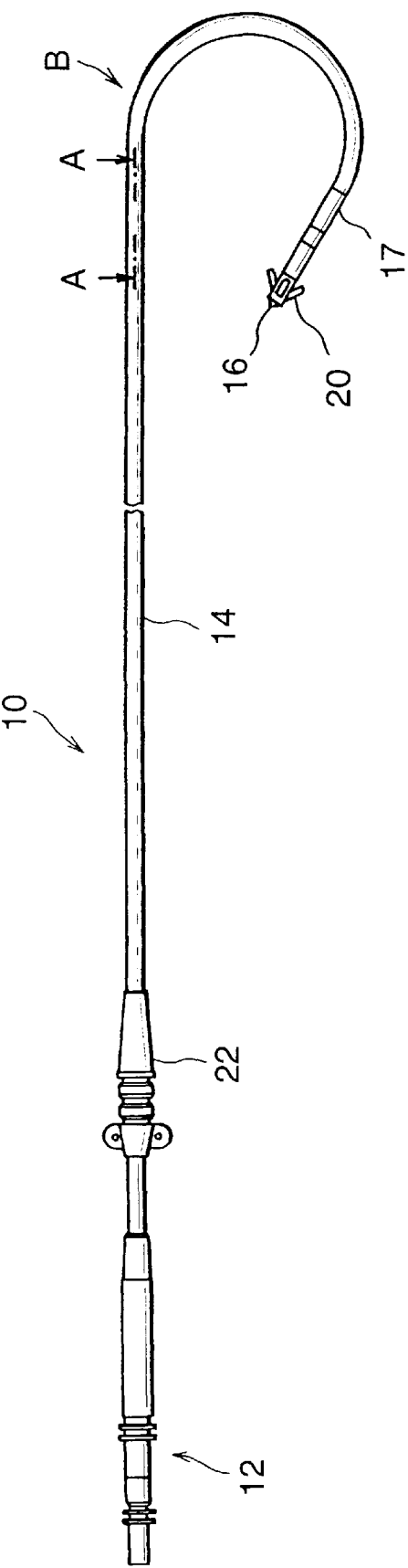
FIG. 2 is a view showing the outer appearance of an atrial lead according to the first embodiment.

FIG. 2 is a front view showing the entire outer appearance of an atrial bipolar lead. Referring to FIG. 2, the atrial lead 10 is mainly comprised of a connector 12, lead body 14, tip electrode 16, and ring electrode 17. A fixing tool 20 is attached near the tip electrode 16 to fix the lead on the endocardium.

A sutural sleeve 22 is attached to the lead body 14 at an illustrated position. To fix the lead body 14 to tissue, the lead body 14 is not directly sutured to the tissue, but the outer surface of the sutural sleeve 22 is sutured to the tissue to protect the lead body 14. A predetermined section near the distal end of the lead body has a J shape, as shown in FIG. 2.

Figure 3:
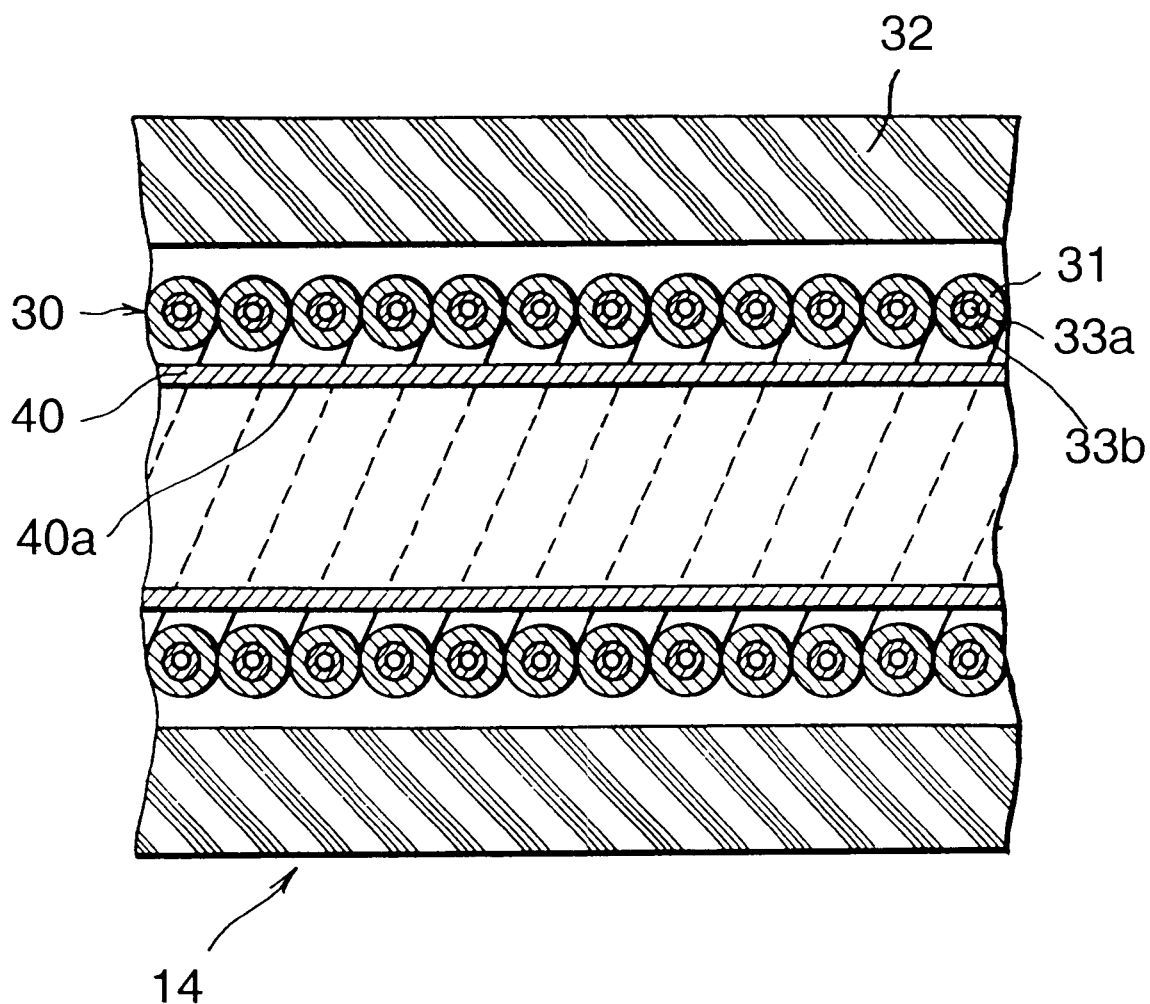
FIG. 3 is a sectional view taken along the line A—A of FIG. 2.

FIG. 3 is a sectional view taken along the line A—A in FIG. 2. The lead body 14 has an insulating parallel winding structure comprised of a coil 30 and an insulating sheath 32 covering the outer surface of the coil and having electrical insulating properties. The coil 30 is formed by helically winding two-layered conductor wires 33a and 33b covered with an insulating coating 31. A flexible reinforcing tube 40 having a cavity 40a for receiving a stylet (to be described later) is fitted in the cavity of the coil 30.

The outer diameter of the lead body 14 is 2 mm or less, and the insulating sheath 32 is made of a flexible, electrically insulating resin material having a Shore hardness of less than 80 A. A spring index D/d (average diameter of coil/diameter of conductor wire) of the coil 30 is preferably set to be larger than 7.8, thereby greatly improving the bending durability of the lead body 14 and at the same time advantageously assuring a large cavity.

The lead body in the conventional bipolar lead generally has a coaxial structure in which the insulating sheath and conductor coil are arranged coaxially. Note that the coaxial structure, however, makes it difficult to form a desired shape when a flexible reinforcing tube is inserted in the cavity (stylet cavity) because the rigidity of the lead body itself is lower than that of the flexible reinforcing tube.

The conductor wire preferably has a composite or cladding structure made up of a first metal material 33a having a low electrical resistivity and a second metal material 33b excellent in corrosion resistance and mechanical characteristics. Examples of this wire structure are DFT (Drawn Filed Tubing) and DSB (Drawn Brazed Strand). It is preferable that silver be used as the first metal material, and a cobalt-based alloy such as MP35N be used as the second metal material.

Figure 4:
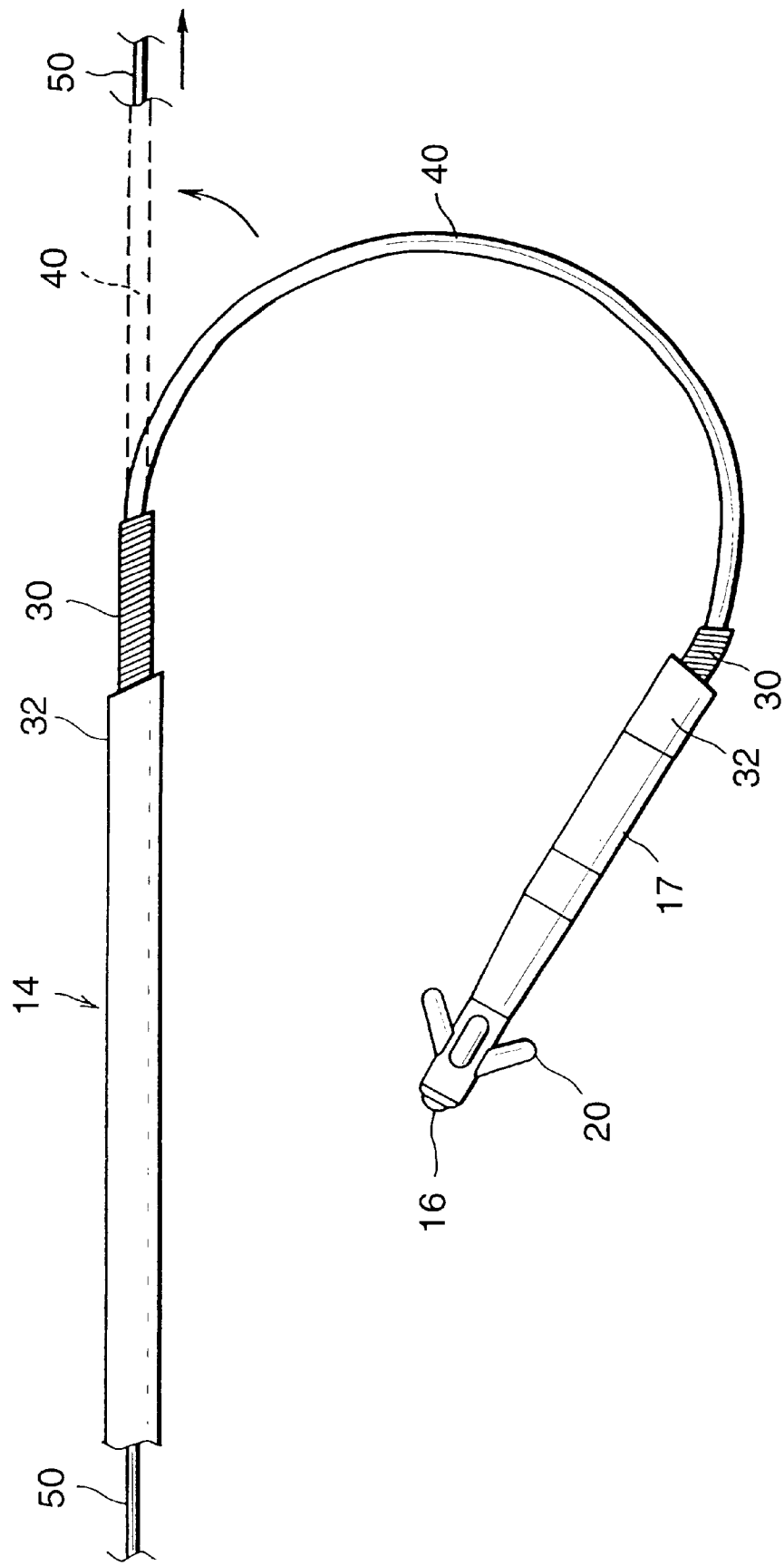
FIG. 4 is a front view showing a state in which a portion B in FIG. 2 is removed.

FIG. 4 is a detailed view showing a state in which a portion B in FIG. 2 is partially removed. Referring to FIG. 4, the flexible reinforcing tube formed into a J shape is disposed in the cavity of the coil 30. This allows maintaining the J shape of the lead body 14 and increasing the retaining force for the J shape.

The material of the flexible reinforcing tube 40 is preferably a relatively hard resin material. Polyimide is selected as the material of the flexible reinforcing tube 40. A stylet 50 can be inserted into the cavity of the flexible reinforcing tube 40. In implanting the lead, the stylet 50 is inserted to the distal end of the lead body 14 to deform the lead body 14 into a straight shape, as indicated by the dotted line in FIG. 4. The stylet 50 is retracted toward the proximal end side upon indwelling the fixing tool 20 in a desired portion, so that the lead body 14 restores the original J shape.

The flexible reinforcing tube 40 has a cavity and disposed in the cavity of the coil 30. There is a very low possibility of the end face of the flexible reinforcing tube 40 boring into the lead body 14 to the outside through the coil 30 and insulating sheath 32.

Figure 5:
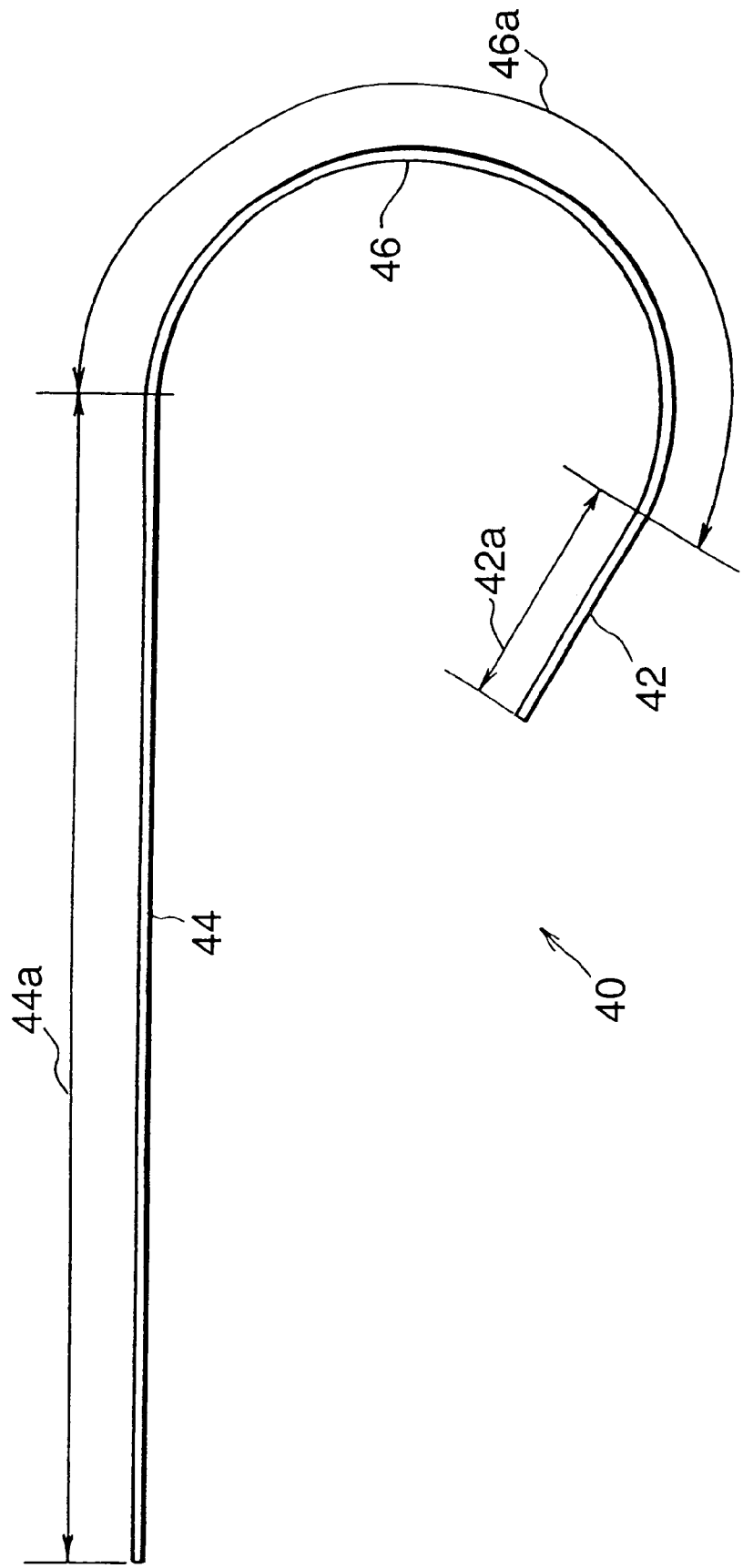
FIG. 5 is a front view of a flexible reinforcing tube.

FIG. 5 is a front view of the flexible reinforcing tube 40. As shown in FIG. 5, the flexible reinforcing tube 40 is made up of a straight portion 42 indicated by an arrow 42*a* starting from the distal end, a straight portion 44 indicated by a proximal-end arrow 44*a*, and an arcuate portion 46 indicated by an arrow 46*a* located between the distal end and proximal end, thereby forming a J shape. The straight portion 42 preferably has a length within the range of 0 mm to 50 mm; and the straight portion 44, 10 mm to 100 mm. The arcuate portion 46 preferably has a radius within the range of 2 mm to 20 mm. The curvature of the arcuate portion 46 may continuously or discontinuously change.

The distal end of the flexible reinforcing tube 40 can be connected to the distal end of the lead body 14, and the proximal end of the flexible reinforcing tube 40 may be connected to the end of the lead body 14. In this manner, the flexible reinforcing tube 40 can extend throughout the lead body 14. This increases the rigidity of the entire lead body. Since the rigidity of the lead body is uniformly distributed, the stylet can be very easily guided to the portion having a desired shape.

In a state prior to assembly of the implantable electrode lead of this embodiment, the shape of the flexible reinforcing tube 40 is not necessarily the same as the desired shape required for the finished product. That is, the flexible reinforcing tube 40 may be combined with the insulating sheath 32 and coil 30, and the resultant structure may be formed into a desired shape.

The bending rigidity of the insulating sheath 32 and coil 30 is determined to be much lower than that of the flexible reinforcing tube 40 to easily obtain a desired shape of the lead body 14. That is, unlike the conventional case, the insulating sheath 32 and coil need not be formed into a desired shape beforehand. Alternatively, the insulating sheath 32 and coil 30 are formed into a desired shape at a portion where the flexible reinforcing tube 40 is located. This can increase the shape-retaining force.

Since the flexible reinforcing tube 40 is made of a resin, its rigidity inevitably decreases upon receiving long-term bending stress in the living body. However, no problem is posed even with a decrease in rigidity due to the following reason. The implantable electrode lead implanted in the living body for a long period of time is covered with tissue around the fixing tool 20, and movement and removal of the electrode can be prevented accordingly.

The flexible reinforcing tube 40 can be made of a thermoplastic resin material. In this case, in the assembly process, the flexible reinforcing tube 40 is set in the coil 30 in a straight state. In one or both of during and after the assembly, the thermoplastic reinforcing tube can be heat-treated to impart a desired shape to the lead body.

[Second Embodiment]

Figure 6:
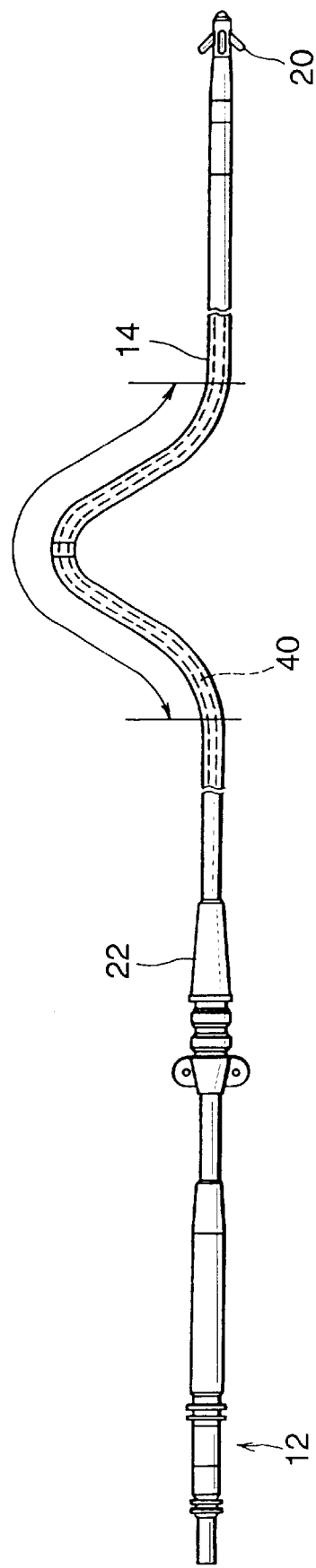
FIG. 6 is a view showing the outer appearance of an implantable electrode lead according to the second embodiment.

As in the first embodiment, a desired shape can be formed intermediate portion along a lead body 14, as shown in the front view of FIG. 6. This can facilitate contact between the electrode and the cardiac muscle in a single lead or the like.

As many apparently widely different embodiments of the present invention can be made without departing from the spirit and scope thereof, it is to be understood that the invention is not limited to the specific embodiments thereof except as defined in the appended claims.

As described above, according to the present invention, a desired portion of the lead body of a flexible, thin implantable electrode lead can be formed into a desired shape. The reinforcing tube serving as the reinforcing means is comprised of a flexible tube and disposed in the cavity of the coil. The flexible tube can be prevented from boring into the insulating sheath to the outside. The reinforcing tube is formed into a J shape for an atrial lead. This can improve operability of the atrial lead and prevent movement and removal of the electrode upon surgical operation.

As has been described above, according to the present invention, there can be provided a flexible, thin implantable electrode lead capable of maintaining a desired portion of the lead body in a desired shape.

What is claimed is:

1. An implantable electrode lead having a lead body for performing at least one of transmission of an electrical stimulation pulse generated by an implantable device to a living body and transmission of an electrical signal from the living body to the implantable device, said lead body having at least one electrode at a distal end thereof, a connector for mechanically and electrically connecting a proximal position of said lead body at an opposite end of said lead body from said at least one electrode to the implantable device, wherein said lead body comprises a conductor coil, said conductor coil being formed from a helical winding of insulation-coated electrical conduction wire, said electrical conduction wire being a multi-layered wire, and said helical winding defining a central cavity of said conductor coil, and an outer surface of said conductor coil being covered by an insulating sheath made of an electrically insulating resin material, a flexible reinforcing tube shaped to deform into a desired shape and being positioned in said central cavity of said conductor coil, said flexible reinforcing tube having a rigidity that is greater than a rigidity of a combination of said conductor coil and said insulating sheath such that said flexible reinforcing tube maintains a predetermined portion of said lead body in the desired shape, said lead body having a size not more than 2 mm, the resin material of which said insulating sheath is made being a flexible material having a Shore hardness of less than 80A, said conductor coil having a spring index D/d of more than 7.8, wherein D/d represents average diameter of coil/diameter of conductor wire, said conductor coil comprising a multi-wire coil obtained by winding a plurality of insulation-coated conductor wires in the same average diameter, and said electrode being divided into a plurality of electrode portions, with one of the wires of said multi-wire coil transmitting one electrical signal and remaining wires of said multi-wire coil transmitting remaining electrical signals.

2. The lead according to claim 1, wherein the predetermined portion is located near a distal end of said lead body, and the desired shape is a substantially J shape.

3. The lead according to claim 1, wherein said reinforcing tube is made of a predetermined resin material containing polyimide.

4. The lead according to claim 1, wherein said reinforcing tube is adapted to be formed into said desired shape before being positioned in said central cavity of said conductor coil.

5. The lead according to claim 1, wherein said reinforcing tube is adapted to be positioned in said central cavity of said coil in a straight state, and shaped to obtain the desired shape after being positioned in said central cavity.

6. The lead according to claim 1, wherein the distal end of said reinforcing tube is connected to said electrode, and a proximal end of said reinforcing tube is connected to said connector.

7. The lead according to claim 1, wherein the insulation coating of said at least one insulation-coated electrical conduction wire is made of fluoroplastic.

8. The lead according to claim 1, wherein said conductor wire has a composite or cladding structure, said composite or cladding structure comprising a first metal material having a relatively low electrical resistivity and a second metal material having excellent corrosion resistance and mechanical characteristics.

9. The lead according to claim 1, wherein said flexible reinforcing tube comprises a cavity, said cavity being adapted for receiving a straight stylet that is inserted into the cavity to deform the desired shape of the predetermined portion of said lead body into a linear shape, and the desired shape being restored by removing said stylet.

10. An implantable electrode lead having a lead body for performing at least one of transmission of an electrical stimulation pulse generated by an implantable device to a living body and transmission of an electrical signal from the living body to the implantable device, said lead body having at least one electrode at a distal end thereof, a connector for mechanically and electrically connecting a proximal position of said lead body at an opposite end of said lead body from said at least one electrode to the implantable device, wherein said lead body comprises a conductor coil, said conductor coil being formed from a helical winding of at least one insulation-coated electrical conduction wire, said electrical conduction wire being a multi-layered wire and said helical winding defining a central cavity of said conductor coil, and an outer surface of said conductor coil being covered by an insulating sheath made of an electrically insulating resin material, a flexible reinforcing tube shaped to deform into a desired shape and being positioned in said central cavity of said conductor coil, said flexible reinforcing tube having a rigidity that is greater than a rigidity of a combination of said conductor coil and said insulating sheath such that said flexible reinforcing tube maintains a predetermined portion of said lead body in the desired shape, said lead body having a size not more than 2 mm, the resin material of which said insulating sheath is made being a flexible material having a Shore hardness of less than 80A, said conductor coil having a spring index D/d of more than 7.8, wherein D/d represents average diameter of coil/diameter of conductor wire, said conductor coil comprising a multi-wire coil obtained by winding a plurality of insulation-coated conductor wires in the same average diameter, and said electrode being divided into a plurality of electrode portions, with one of the wires of said multi-wire coil transmitting one electrical signal and remaining wires of said multi-wire coil transmitting remaining electrical signals.

11. The lead according to claim 10, wherein said reinforcing tube is made of a predetermined resin material containing polyimide, and said reinforcing tube is adapted to be formed into the desired shape before being positioned in the central cavity of the conductor coil.

12. The lead according to claim 10, wherein said reinforcing tube is adapted to be positioned in the central cavity of said coil in a straight state, and shaped to obtain the desired shape after being positioned in the central cavity.

13. The lead according to claim 10, wherein the distal end of said reinforcing tube is connected to said electrode, and a proximal end of said reinforcing tube is connected to said connector.

14. The lead according to claim 10, wherein said lead body has a size of not more than 2 mm, said insulating sheath is made of an electrically insulating, flexible resin material having a Shore hardness of less than 80A, and said conductor coil has a spring index D/d (average diameter of coil/diameter of conductor wire) of more than 7.8.

* * * * *